(12) United States Patent
Kolbe et al.

(10) Patent No.: US 6,957,567 B2
(45) Date of Patent: Oct. 25, 2005

(54) METHOD AND SYSTEM FOR THE CONTROLLED APPLICATION OF FLUID PRESSURE TO A LOAD, ESPECIALLY FOR PRESSURE TESTING PIPE

(75) Inventors: Manfred Kolbe, Mönchengladbach (DE); Hans-Güntar Schiffers, Mönchengladbach (DE); Uwe Feldmann, Rommerskirchen (DE); Wolfgang Krutz, Mönchengladbach (DE)

(73) Assignee: SMS Meer GmbH, Monchengladbach (DE)

( * ) Notice: Subject to any disclaimer, the term of this patent is extended or adjusted under 35 U.S.C. 154(b) by 0 days.

(21) Appl. No.: 10/624,845

(22) Filed: Jul. 22, 2003

(65) Prior Publication Data

US 2004/0187562 A1 Sep. 30, 2004

(30) Foreign Application Priority Data

Jul. 23, 2002 (DE) ......................... 102 33 358

(51) Int. Cl.$^7$ .......................... G01M 3/04; F04B 35/00
(52) U.S. Cl. ........................................ 73/49.4; 417/345
(58) Field of Search ................. 73/49.4, 49.1, 73/49.5; 138/90; 137/112; 417/344, 345, 346

(56) References Cited

U.S. PATENT DOCUMENTS

| | | | | |
|---|---|---|---|---|
| 1,613,150 | A | * 1/1927 | Zore ........................... | 73/49.4 |
| 2,442,916 | A | * 6/1948 | Buchanan .................... | 417/346 |
| 2,660,955 | A | * 12/1953 | Kent et al. ..................... | 91/20 |
| 3,773,438 | A | * 11/1973 | Hall et al. .................. | 417/345 |
| 3,893,790 | A | * 7/1975 | Mayer ......................... | 417/346 |
| 4,021,156 | A | 5/1977 | Fuchs, Jr. et al. | |
| 4,666,374 | A | 5/1987 | Nelson | |
| 4,766,934 | A | * 8/1988 | Ollivaud et al. .............. | 138/90 |
| 4,924,671 | A | * 5/1990 | Reinert ....................... | 417/346 |

FOREIGN PATENT DOCUMENTS

| | | |
|---|---|---|
| FR | 2 689 571 | 10/1993 |
| GB | 2 175 352 | 11/1986 |
| SU | 717 595 | 2/1980 |
| SU | 1029 036 | 7/1983 |

* cited by examiner

Primary Examiner—Michael Cygan
(74) Attorney, Agent, or Firm—Herbert Dubno

(57) ABSTRACT

A method and system for the controlled application of fluid pressure of a load, such as a large pipe to be pressure tested utilized small pressure converters which are operated by a common controller at the hydraulic side to fill and pressurize the pipe. One pressure converter is decelerated as it approaches the end of its working stroke while the other pressure converter is accelerated so that the total displacement of the pressurizing fluid remains substantially constant over time.

5 Claims, 2 Drawing Sheets

US 6,957,567 B2

METHOD AND SYSTEM FOR THE CONTROLLED APPLICATION OF FLUID PRESSURE TO A LOAD, ESPECIALLY FOR PRESSURE TESTING PIPE

FIELD OF THE INVENTION

Our present invention relates to the application of a fluid pressure to a load, especially for pressure testing pipes. More particularly, the invention relates to a method for the controlled buildup of pressure by means of pressure converters, especially for a press for the testing of the pressure tightness of large pipes by filling them with a liquid after closure of their ends and thereby effecting a pressure buildup through pressure converters. A pressure converter for the purposes of the present invention will be understood to be a device which receives a fluid pressure at a drive side and outputs a fluid pressure at an output side, usually with a fluid pressure amplification.

BACKGROUND OF THE INVENTION

The controlled application of fluid pressure to a load utilizing, for example, a pressure converter at whose pressure output side, the pressure converter is connected by one check valve to a source of fluid and by another check valve to the load, utilizes the repeated strokes of the pressure converter to allow a fluid to b drawn into the output side through the first check valve and then to be discharged at higher pressure through the second check valve.

In order to pressurize liquid for pressure testing and like applications, high pressure plunger pumps have generally been used and this is the case for the pressure testing of pipes as well.

Since the reciprocation of the piston for pressurizing the pipe can result in the generation of an oscillation which may represent a deviation from a test protocol, such oscillations cannot be tolerated for pipe-testing purposes. The pressure medium used for the pipe testing is generally water and optionally a water-based emulsion and since a control valve in frequently provided to connect the piston pump with the pipe to be tested, that valve may be subject to wear from substances which may be entrained in the water or water emulsion, like scale or the like.

When pressure converters were provided for the testing of pipe and the like, the pressure regulation could be effected at the oil side of the system to eliminate wear of the control valve by the water or water emulsion. In addition such systems did not have oscillations during pressure buildup and while the pressure was maintained.

However, the volume required at the water side was invariably far in excess of the compression volume of the converter and thus for practical reasons very large and hence expensive pressure converters had to be us d. In addition, the pressure converters gave rise to extreme fluctuations in the pressure medium. These drawbacks not only applied to pipe-testing presses but wherever the unit was used to build up a fluid pressure for a load.

OBJECTS OF THE INVENTION

It is, therefore, the principal object of the present invention to provide an improved control method for the purposes described which allows a pressure buildup so that the drawbacks which have been detailed are eliminated and high pressures can be achieved with a simple and inexpensive apparatus and maintained for long periods of time without difficulty.

It is also an object of the invention to provide a method for the controlled application of fluid pressure to a load which can be utilized especially for testing large diameter pipe with a saving in time and in cost.

Still another object of the invention is to provide a improved system for the controlled application of fluid pressure to the load which is simple to operate, reliable and inexpensive.

SUMMARY OF THE INVENTION

These objects are achieved in accordance with the invention in a method of controlled application of fluid pressure to a load which comprises the steps of:

(a) providing at least two pressure converters each having an output side connectable through respective check valves with a source of a pressurizing fluid and with the load, a drive side pressurizable in opposite directions to draw the fluid into and discharge the fluid from a respective output side, and a connection between each pressure side and the respective output side whereby each pressure converter has a member displaceable by pressurization of the respective drive side;

(b) measuring the displacement of each of the members; and (c) controlling the pressurization of each of the drive sides so as to reduce an output pressure of a respective output side of one of the pressure converters as the respective member approaches a limiting position in a pressure stroke of the one of the pressure converters, and complementarily increasing an output pressure of a respective output side of another of the pressure converters and a displacement of the respective member of the other pressure converter by initiating a pressure stroke of the other pressure converter, i.e. decelerating the one converter while simultaneously accelerating the other before the one converter reaches its limiting position.

The system can comprise:

at least two pressure converters each having an output side connectable through respective check valves with a source of a pressurizing fluid and with the load, a drive side pressurizable in opposite directions to draw the fluid into and discharge the fluid from a respective output side, and a connection between each pressure side and the respective output side whereby each pressure converter has a member displaceable by pressurization of the respective drive side;

a respective displacement measuring device cooperating with each of the members for measuring the displacement of each of the members; and a common control unit for controlling the pressurization of each of the drive sides so as to reduce an output pressure of a respective output side of one of the pressure converters as the respective member approaches a limiting position in a pressure stroke of the one of the pressure converters, and complementarily increasing an output pressure of a respective output side of another of the pressure converters and effecting a displacement of the respective member of the other pressure converter by initiating a pressure stroke of the other pressure converters.

In accordance with the invention, the pressurization of the drive sides is controlled through respective valves and a common controller for the valves receiving inputs from respective position sensors responding to the positions of the members, the method further comprising the step (d) of repeating steps (a) through (c) a plurality of times until a certain pressure is reached at the load.

When the system is to be used to test a pipe, the load is a length of pipe which is closed at its ends and is pressurized by the pressure converter.

According to a feature of the invention a valve is provided between the output sides of the pressure converters and the pipe and enables filling of the pipe under pressure and then draining of the liquid from the pipe. A proportional/integral regulator can be provided between the output sides of the converters and the pipe for delivering a signal to the common controller.

According to a feature of the invention, the pressure converters with their displacement sensors and control valves operated by the common controller form an operating system which, as soon as a first pressure converter approaches its end position, its speed is reduced and a next pressure converter is accelerated so that between the two pressure converters, the output is maintained constant. This process can be repeated as many times as is necessary, each time by reducing the speed of one pressure converter and accelerating the other to bring about a continuous pressure buildup without a discontinuity or over-swing in the pressurization of the load. Since the braking and acceleration are synchronized, the sum of the fluid displacements from the pressure converters during the overlap in their operation can be constant or can correspond to a desired rate of flow to bring about the optimum pressure buildup to the load.

In spite of the use of smaller and less expensive commercially available and structurally identical pressure converters, the high compression volume required for pipe pressure testing can be achieved even for large pipe. As a consequence large and thus expensive pressure converters that have to be especially fabricated for the purpose can be avoided entirely.

The filling and compression volume which must be met are not limited in that multiple and simple and inexpensive small pressure converters can be used alternatingly and the cycling between the two can be repeated as often as required to build up the requisite large volume and pressure. A pressure sensor can be provided for the control unit which can pick up the internal pressure of the pipe and cause the controller to operate repeatedly until a setpoint pressure is reached. In addition, high useful lives of the control valve can be achieved since they need not be exposed to the water. The valves are located, according to the invention on the oil hydraulic pressurization side rather than the output side of the pressure converters.

The pressure converters can also be used for the decompression of the pipes and to permit the discharge of the pressure fluid therefrom.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
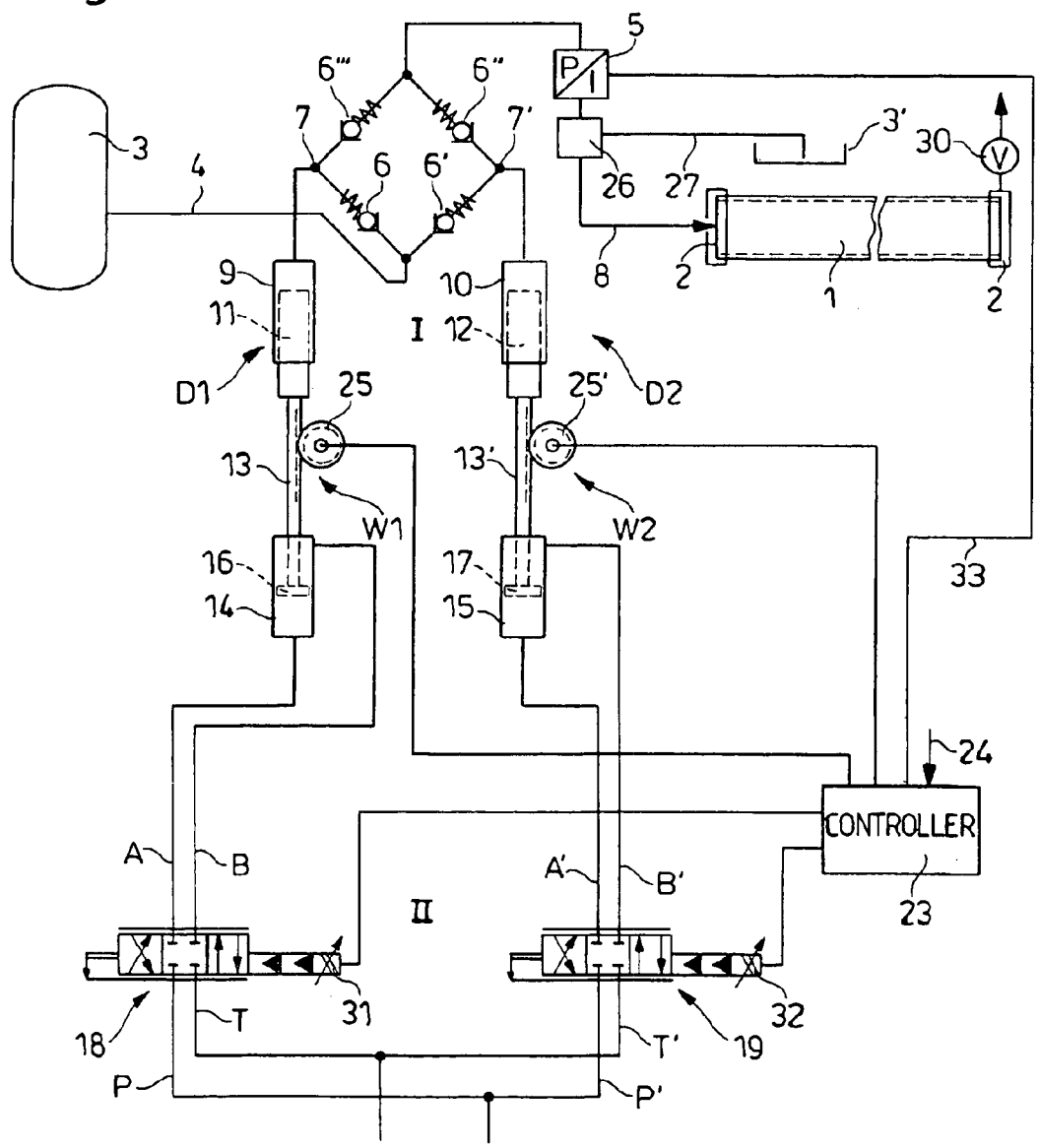
FIG. 1 is a flow diagram illustrating the system according to the invention for pressure testing a pipe.

FIG. 1 shows large diameter pipe to be pressure tested and represents at 2 caps or plugs adapted to close this pipe. One of these plugs may be provided with a vent valve 30 which may be opened to the atmosphere for filling the pipe with the pressurizing liquid, e.g. a water-oil emulsion, and for discharging the emulsion from the pipe.

A pressure tank 1 serves to supply the pressurizing medium and, of course, some other source of the pressurizing medium can be used as well. Typical other potential sources include nonpressurized vessels, centrifugal pumps or the like.

A tank 3' can receive the pressurizing fluid discharged from the pipe 1.

A valve 26 can feed the pressurized liquid via line 8 to the pipe 1 or discharge the liquid via line 27 to the tank 3' when the pressure converters are not used to empty the pipe 1. Alternatively, the pipe 1 may be filled from tank 3' by gravity so that the pressure converters only elevate the pressure in the pipe 1 to the test pressure.

The pressure converters are represented at D1 and D2 and at least two such pressure converters are provided. The pressure converters have a water side I and an oil or hydraulic medium side II as represented in FIG. 1. The output sides of the pressure converters D1 and D2 are formed by cylinders 9 and 10 and plungers or pistons 11 and 12. Each of the plungers or pistons 11, 12 is driven via a rod 13 or 13' by a piston 16 or 17 of a drive cylinder 14 or 15. The drive cylinders 14 and 15 are double-acting cylinders.

At the output sides of the pressure converters, the cylinders 9 and 10 are connected at points 7 and 7' to a bridge of check valves 6, 6', 6", 6'".

On the intake stroke, the piston 11 is retracted from the cylinder 9 of the pressure converter D1 and the pressurizing medium, i.e. the water-oil emulsion is drawn from tank 3 through check valves 6 into the cylinder 9. On the pressure stroke, the piston 11 is driven into the cylinder 9 and the pressurizing liquid is driven via the check valve 6'" through the proportional-integral regulator 5 and valve 26 into the pipe 1.

Similarly, on the intake stroke, the piston 12 is drawn from the cylinder 10 and the pressurizing liquid passes from tank 3 via check valve 6' into the cylinder 10. It is expressed from the cylinder through check valve 6" upon the pressure stroke to the pipe 1.

The drive cylinders 16 and 17 are each connected with a 4-port, 3-position valve 18, 19, two ports of which are connected by lines A and B or A' and B' to the opposite ends of the cylinders 14 and 15. The other two ports of each of the valves 18 and 19 are connected to a pressure pump via lines P and P' and to a return tank by lines T and T'.

A common controller 23 transmits electrical signals to the electrical effectors 31 and 32 of the valves 18 and 19. The output of the proportional-integral regulator is applied to the controller via line 33.

For the pressure buildup in the pipe 1, initially the pressure converter D1 is actuated and the pressurizing liquid drawn from the tank 3 is displaced via electric valve 6'" in the pressure or working stroke of the plunger 11 to block the electric valve 6 and open the electric valve 6'" so that the pressurizing liquid passes via line 8 into the pipe 1. Shortly before the plunger 11 terminates its working stroke and reacher its end position and as the plunger 11 approaches its end position, the plunger 12 of the second pressure convertor D2 is set in motion to build up the pressure in cylinder 10 and drive the pressurizing fluid via check valve 6" to the pipe 1. The pressure converters are alternatingly operated in this manner, filling the cylinder 9 and 10 and driving the fluid into pipe 1 until the final compression volume is reached. The proportional-integral regulator 5 monitors the pressure buildup and terminates that buildup when the desired pressure has been reached by operating the controller 23. The pressure converter which is not active at any time for buildup of pressure can be reversed for intake from the tank 3.

The drives for the plungers 11, 12 are the piston and cylinder units 14, 16 and 15, 17 which are coupled via the rods 13, 13' with the plungers.

In the position shown for the valves 18 and 19, the piston and cylinder units 14, 16 and 15, 17 are stationary. When the valves 18 and 19 are shifted to the left, the lower cylinder compartments are pressurized and the plungers 11 and 12 have their working strokes. When the valves are shifted to the right, the upper compartments are pressurized and the plungers 11 and 12 have their intake strokes.

Figure 2:
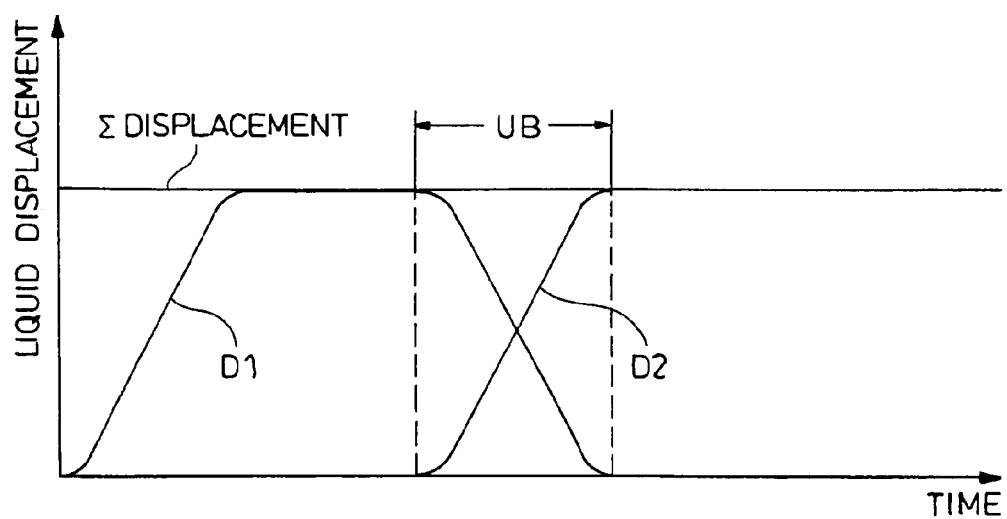
FIG. 2 is a graph of the liquid displacement versus time, illustrating the invention.

The rods 13 and 13' are formed as racks which mesh with pinions 25 and 25' forming the displacement measurement sensors W1 and W2 which provide inputs to the controller 23. The controller can thus respond to the proximity of the plungers 11 and 12 to their end positions to reduce the speed of the respective plunger of one of the pressure converters and accelerate the plunger of the other so that, as shown in FIG. 2, over the time period UB, the displacement of the pressurizing liquid from converter D1 falls at the same rate as the displacement from the converter D2 increases so that the total displacement to the pipe 1 remains constant. An input 24 provides a setpoint for the controller 23. The cycling between two pressure converters is repeated until the desired pressure is reached.

It thus will be apparent that even for pressure testing of large pipes, the comparatively large filling volume and compression volume can be reached with relatively small conventional pressure converters by operating them with a common controller alternately in such manner that the displacement is at a substantially constant rate and thus no pressure fluctuation or oscillation can arise.

We claim:

1. A system for controlled application of fluid pressure to a load in the form of a pipe closed at its ends to pressure test the pipe, said system, comprising:
   at least two pressure converters each having an output side connectable through respective check valves with a source of a pressurizing fluid and with said load, a drive side pressurizable in opposite directions to draw said fluid into and discharge said fluid from a respective output side, and a connection between each pressure side and the respective output side whereby each pressure converter has a member displaceable by pressurization of the respective drive side;
   a respective displacement measuring device cooperating with each of said members for measuring the displacement of each of said members;
   a common control unit for controlling the pressurization of each of said drive sides so as to reduce an output pressure of a respective output side of one of said pressure converters as the respective member approaches a limiting position in a pressure stroke of said one of said pressure converters, and simultaneously increasing an output pressure of a respective output side of another of said pressure converters and effecting a displacement of the respective member of said other pressure converter by initiating a pressure stroke of said other pressure converters, the pressurization of said drive sides being controlled through respective valves and a common controller for said valves forming said control unit and receiving inputs from respective displacement measuring devices responding to the positions of said members, the pressure strokes being repeated until a certain pressure is reached at said load; and
   proportional/integral regulator between said output sides and said pipe for delivering a signal to said common controller.

2. The system defined in claim 1 wherein said output sides are connected to said pipe through a valve enabling draining of said pipe following a test.

3. The system defined in claim 1 wherein each of said pressure converters has at said drive side a respective double-acting cylinder and a piston, each of said output sides has a respective cylinder and piston and the respective member of each of said pressure converters connects the pistons to the cylinders thereof.

4. A system for controlled application of fluid pressure to a load in the form of a pipe closed at its ends to pressure test the pipe, said system, comprising:
   at least two pressure converters each having an output side connectable through respective check valves with a source of a pressurizing fluid and with said load, a drive side pressurizable in opposite directions to draw said fluid into and discharge said fluid from a respective output side, and a connection between each pressure side and the respective output side whereby each pressure converter has a member displaceable by pressurization of the respective drive side;
   a respective displacement measuring device cooperating with each of said members for measuring the displacement of each of said members;
   a common control unit for controlling the pressurization of each of said drive sides so as to reduce an output pressure of a respective output side of one of said pressure converters as the respective member approaches a limiting position in a pressure stroke of said one of said pressure converters, and simultaneously increasing an output pressure of a respective output side of another of said pressure converters and effecting a displacement of the respective member of said other pressure converter by initiating a pressure stroke of said other pressure converters, the pressurization of said drive sides being controlled through respective valves and a common controller for said valves forming said control unit and receiving inputs from respective displacement measuring devices responding to the positions of said members, the pressure strokes being repeated until a certain pressure is reached at said load; and
   each of said pressure converters has at said drive side a respective double-acting cylinder and a piston, each of said output sides has a respective cylinder and piston and the respective member of each of said pressure converters connects the pistons to the cylinders thereof, each of said members being a rack and said displacement measuring devices including pinions engageable with said racks.

5. The system defined in claim 4 wherein each of said double-acting cylinders is connected to two ports of a four-port, three position valve having two further ports connected to a hydraulic pressure source and drain respectively, each of said four-port, three-position valves having an electrical actuator operated by said common controller.

* * * * *